(12) United States Patent
Prutchi et al.

(10) Patent No.: US 8,901,878 B2
(45) Date of Patent: Dec. 2, 2014

(54) TRANSCUTANEOUS CHARGING DEVICE

(75) Inventors: David Prutchi, Voorhees, NJ (US); Paul Richard Spehr, Medford, NJ (US)

(73) Assignee: Impulse Dynamics NV, Curacao, Dutch Caribbean ( * ) Notice: Subject to any disclaimer, the term of this patent is extended or adjusted under 35 U.S.C. 154(b) by 1333 days.

(21) Appl. No.: 12/155,448

(22) Filed: Jun. 4, 2008

(65) Prior Publication Data

US 2008/0303480 A1  Dec. 11, 2008

Related U.S. Application Data

(60) Provisional application No. 60/924,920, filed on Jun. 5, 2007.

(51) Int. Cl.
*H02J 7/00* (2006.01)
*H02J 7/02* (2006.01)
*A61N 1/378* (2006.01)

(52) U.S. Cl.
CPC .............. *H02J 7/025* (2013.01); *A61N 1/3787* (2013.01)
USPC ........... 320/107; 320/108; 320/114; 320/137; 320/150; 320/155

(58) Field of Classification Search
USPC ................... 320/107, 114, 137, 155
See application file for complete search history.

(56) References Cited

U.S. PATENT DOCUMENTS

| 5,411,537 | A | * | 5/1995 | Munshi et al. | 607/33 |
|---|---|---|---|---|---|
| 5,702,431 | A | * | 12/1997 | Wang et al. | 607/61 |
| 5,733,313 | A | * | 3/1998 | Barreras et al. | 607/61 |
| 8,346,361 | B2 | * | 1/2013 | Bauhahn et al. | 607/33 |
| 2002/0140399 | A1 | * | 10/2002 | Echarri et al. | 320/130 |
| 2005/0022181 | A1 | * | 1/2005 | Fox et al. | 717/174 |
| 2005/0075696 | A1 | * | 4/2005 | Forsberg et al. | 607/61 |
| 2006/0025828 | A1 | * | 2/2006 | Armstrong et al. | 607/28 |
| 2007/0067004 | A1 | * | 3/2007 | Boveja et al. | 607/45 |
| 2007/0150019 | A1 | * | 6/2007 | Youker et al. | 607/29 |
| 2007/0255235 | A1 | * | 11/2007 | Olsen et al. | 604/288.01 |
| 2008/0262379 | A1 | * | 10/2008 | Gerber et al. | 600/549 |
| 2011/0015701 | A1 | * | 1/2011 | KenKnight et al. | 607/60 |
| 2011/0077720 | A1 | * | 3/2011 | Torgerson et al. | 607/61 |
| 2011/0301669 | A1 | * | 12/2011 | Olson et al. | 607/61 |

\* cited by examiner

*Primary Examiner* — Bot Ledynh

(57) ABSTRACT

A transcutaneous charging device for charging an implant comprising:
  a power input;
  a conversion circuit to convert power from said power input to transcutaneously charge said implant;
  a control; and
  an indication element;
  wherein said control is programmed to initiate an indication using said indication element when it is time to charge said implant.

20 Claims, 4 Drawing Sheets

TRANSCUTANEOUS CHARGING DEVICE

RELATED APPLICATIONS

This application claims the benefit of priority from U.S. Provisional Patent Application No. 60/924,920 filed on Jun. 5, 2007, the contents of which are incorporated by reference as if fully set forth herein.

FIELD OF THE INVENTION

The present invention relates to transcutaneous charging of an implantable medical device.

BACKGROUND OF THE INVENTION

It is common practice in the field of medicine to implant electronic devices inside the human body in order to overcome various problems, for example a pacemaker, a defibrillator or an infusion pump. Such devices require a power source for the device to monitor the body and optionally, perform a remedial function. For some devices, power for the device is supplied by a rechargeable battery that can be recharged transcutaneously so that additional operations on the patient are not needed in order to replenish the electrical power source.

Some types of rechargeable batteries (e.g. Nickel-Cadmium) suffer from memory effects, which require charging them when they reach a certain level of depletion, in order to prevent damage to their ability to hold a charge. Newer batteries (e.g. Lithium-Ion) can be charged at the convenience of a user (either a patient, or someone else responsible), for example periodically. In either case the user needs to keep track of the charge status of the battery to assure that the battery has enough charge to function if needed. If the user overestimates the available charge the result could be fatal, depending on the application.

Implanted devices are typically placed in an enclosure made of a bio-compatible metal material, to protect the device, and to protect the patient from leakage from the device. One problem with using such a metal enclosure is that it may heat up as a result of eddy currents caused by a time-varying electromagnetic field, for example when charging the device. Generally the heat dissipates through surrounding tissue and the blood flow. However when transcutaneously charging a battery by induction, the implant may heat up faster than it can dissipate the excess heat. High temperatures (e.g. above 42° C.) can damage surrounding tissue. As a result, charging the battery is typically performed at a low rate to prevent harm to the patient.

U.S. Pat. No. 5,991,665 describes a self cooling transcutaneous energy transfer system, wherein a fan is used to cool the skin at the charging point in order to allow a faster charge rate.

US 2005/0075696 describes an inductive charger for an implant, in which various means are used to detect when the primary and secondary coils are not optimally aligned, including measuring the power load on the primary load.

SUMMARY OF THE INVENTION

An aspect of some embodiments of the invention relates to an implant and a transcutaneous charging device that complement each other to enhance safety of a patient while optionally speeding up the charging process.

In an exemplary embodiment of the invention, the charging device provides an indication of when the implant should be charged in order to prevent the user from forgetting to charge the device. Optionally, charger 110 gives such indication periodically or at set time intervals. In some embodiments of the invention, after completing the process of recharging, the implant notifies the charging device to update its records and/or reset a counter.

In some embodiment of the invention, the implant keeps track of its current temperature during the charging process and suspends the process if the temperature exceeds a preselected value (e.g. a temperature that could cause harm to the patient).

In some embodiments of the invention, a high charge rate is selected to transfer charge intermittently instead of transferring charge at a low rate continuously.

In some embodiments of the invention, the charging device is shielded with a cold water pad which is in contact with the patient's skin during the charging process. Optionally, the cold water pad and automatic charge suspension allow the charging device to transfer charge at an overall faster rate without overheating the patient. Additionally, the cold water pad lengthens the time interval available for charging the implant before the implant suspends the charging process and waits for the temperature to go down. In some embodiments of the invention, the charging device gives an indication that it is suspended to allow a user to replace the pad with a fresh cooled pad. (As used herein, "user" will refer either to the patient who has the implant, or to someone else responsible for keeping the implant charged.)

In some embodiments of the invention the charging device is coupled with a dynamic cooling pad in which cooled water flows in and out of the pad.

There is thus provided, in accordance with an exemplary embodiment of the invention, a transcutaneous charging device for charging an implant comprising:

a power input;

a conversion circuit to convert power from said power input to transcutaneously charge said implant;

a control; and an indication element;

wherein said control is programmed to initiate an indication using said indication element when it is time to charge said implant.

Optionally, the device comprises a wireless receiver and said indication is stopped after deploying said charger and receiving a signal from said implant by said wireless receiver.

Optionally, said indication is initiated periodically.

Optionally, said indication is initiated on specific dates.

Optionally, said indication, when activated, is continuous.

Alternatively, said indication, when activated, is intermittent.

Optionally, said signal is supplied by said implant after it is recharged.

Optionally, said indication element comprises a display.

Alternatively or additionally, said indication element comprises an audio transmitter.

Alternatively or additionally, said indication element comprises a mobile telephone transmitter.

In an embodiment of the invention, the device comprises a battery backup.

There if further provided, in accordance with an exemplary embodiment of the invention, a transcutaneous charging device for charging an implant comprising:

a power input;

a conversion circuit that converts power supplied by said power input to transcutaneously charge said implant;

a control; and a wireless receiver that is adapted to receive a signal from the implant;

wherein the control is adapted to suspend transfer of charge responsive to said signal.

Optionally, said signal from said implant is transmitted if the temperature sensed in the implant exceeds a threshold temperature.

Optionally, the threshold temperature is at least 39° C.

Optionally, said control resumes transfer of charge responsive to lack of a signal from said implant.

Additionally or alternatively, said control resumes transfer of charge responsive to a second signal from said implant.

Optionally, the device comprises a liquid filled cooling pad shielding between said conversion circuit and a user.

Optionally, said liquid in said cooling pad is cooled by an external cooler.

Optionally, said signal from said implant is transmitted if the implant is fully charged.

There if further provided, in accordance with an exemplary embodiment of the invention, a method of transcutaneously charging a battery of an implant in a person comprising:

deploying a charger;

transcutaneously charging the battery of the implant with the charger;

suspending and resuming the charging responsive to a signal from said implant.

Optionally, said signal from said implant gives an indication of the temperature of the implant.

Optionally, said signal from said implant gives an indication of the charge status of the battery of the implant.

In an embodiment of the invention, deploying the charger comprises placing a liquid filled cooling pad shielding between the charger and the person.

Optionally, the method comprises cooling said liquid in said cooling pad by an external cooler.

Optionally, said charging is at a rate greater than 25% of a maximum charging rate of the battery.

Optionally, said charging is at a rate greater than 50% of the maximum charging rate of the battery.

Optionally, the method comprises supplying an indication to a user that it is time to charge the battery.

BRIEF DESCRIPTION OF THE DRAWINGS

Particular exemplary embodiments of the invention will be described with reference to the following description of embodiments in conjunction with the figures, wherein identical structures, elements or parts which appear in more than one figure are generally labeled with a same or similar number in all the figures in which they appear, in which.

DETAILED DESCRIPTION OF EXEMPLARY EMBODIMENTS

Figure 1:
FIG. 1 is a schematic illustration of deploying a transcutaneous charge system comprising a charger and an implant, according to an exemplary embodiment of the invention.

FIG. 1 is a schematic illustration of a transcutaneous charge system 100 comprising a charger 110 and an implant 120, for example a pacemaker, deployed according to an exemplary embodiment of the invention. Typically, implant 120 is implanted in a patient during a medical operation. In an exemplary embodiment of the invention, charger 110 is placed on the patient's skin facing implant 120 in order to transcutaneously recharge a power source in implant 120.

In an exemplary embodiment of the invention, charger 110 is placed on the skin in a location as close as possible to implant 120. In some embodiments of the invention, a separation is placed between charger 110 and the skin, for example a piece of material or a towel. The separation makes the touch of the charger more comfortable and protects the patient from heat in the charger. Optionally, a cooled pad 130 (e.g. a cooled water pad) is placed between the skin and charger 110 in order to alleviate the effect of heating from implant 120 and/or charger 110 during the charging process. Optionally, by introducing a cold element (e.g. pad 130) in contact with the skin near the position of the implant, charger 110 is able to transfer charge at a higher rate and/or for a longer time before needing to suspend charging to prevent overheating. In some embodiments of the invention, the user can replace pad 130 with a new pad if the temperature of the pad reaches a level that causes it to stop being effective as a cooling element.

Optionally, pad 130 is comprised from a material of low conductivity and/or low magnetic permeability in order to minimize disturbance to the charge signal.

Figure 2:
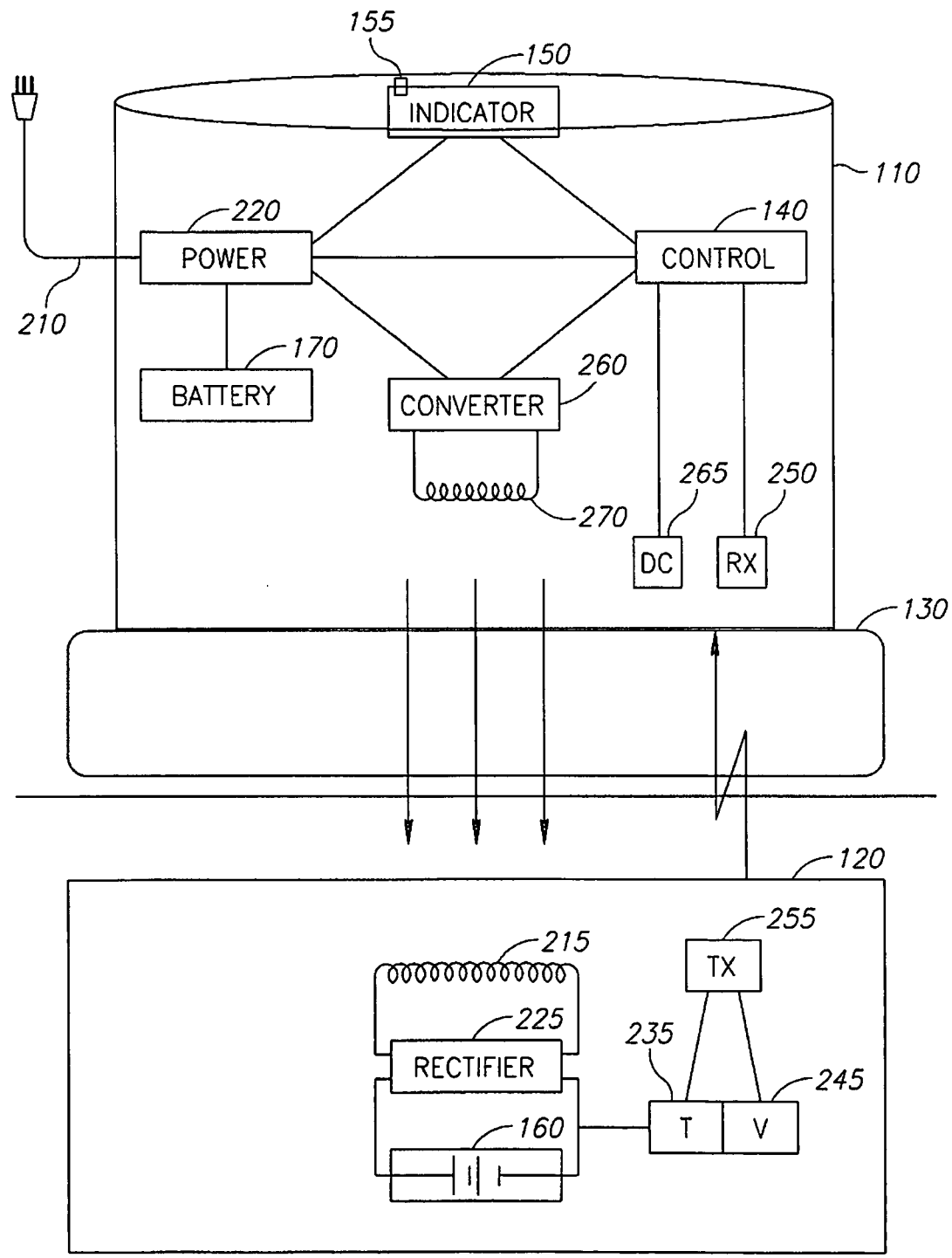
FIG. 2 is a simplified schematic block diagram of circuit elements for implementing the transcutaneous charge system, according to an exemplary embodiment of the invention.

FIG. 2 is a schematic diagram of circuit elements for implementing the transcutaneous charge system 100, according to an exemplary embodiment of the invention. In an exemplary embodiment of the invention, implant 120 comprises a rechargeable battery 160, which is optionally initially charged when implant 120 is installed. In an exemplary embodiment of the invention, charger 110 comprises a control 140 with a timer, to keep track of the time that elapsed the last charging of battery 160. Optionally, control 140 is programmed to instruct an indicator 150 to give an indication, for example an audio signal (e.g. a continuous beep) or a viewable signal (e.g. a flashing or steady light, from a light source such as a LED), until the user deploys charger 110 and recharges battery 160. In some embodiments of the invention, charger 110 sends a wireless signal, for example using a mobile telephone included in indicator 150 to call the patient and transmit a reminder message.

In some embodiments of the invention, control 140 is programmed to give an indication after a set time interval, for example every 4 months. Alternatively control 140 is programmed to give indication on specific days for example the first day of every other month or on the first Sunday of every month. In some embodiments of the invention, the user is required to deploy charger 110 periodically, for example once a month in order to check the charge status of implant 120. Optionally, charger 110 gives the user an estimate of when charging will be required. In some embodiments of the invention, charger 110 gives an estimate of the time required for charging implant 120, based on the charge level, so that a patient can plan his or her day.

In some embodiments of the invention, charger 110 comprises a battery 170 to supply backup power for control 140 and indicator 150, since they need to function even when charger 110 is not plugged into a power source to charge battery 160. Optionally, battery 170 may be a standard non-rechargeable battery, which is changed when depleted. Optionally, charger 110 gives an indication if battery 170 is nearly depleted (e.g. a LED is lit). In some embodiments of the invention, battery 170 is also rechargeable. Optionally, battery 170 is recharged when charger 110 is plugged in and deployed to recharge battery 160 of implant 120.

In some embodiments of the invention, battery 170 is rechargeable, and is used to recharge battery 160 of implant 120, without the need to plug in charger 110 when battery 160 is recharged. In these embodiments, charger 110 is fully portable, and need not be near a wall outlet when it is operating to recharge battery 160. Instead, charger 110 is plugged into a wall outlet at any convenient time, to recharge battery 170.

In some embodiments of the invention, indicator 150 comprises an input device 155 (e.g. a switch) to enable the user to turn off the indication. Alternatively or additionally, the indication is turned off when the charger is deployed and communicates with the implant, for example as shown in FIG. 1. Optionally, the indicator is turned off during charging of the implant, but will continue to give the indication or a different indication if the charging process is not completed and confirmation received from implant 120. In some embodiments the color of a LED changes to represent the status, for example red before charging, yellow while charging and green after charging.

In some embodiments of the invention, battery 160 lasts for a longer time if intervention of implant 110 is not required than if intervention of implant 110 is required, for example a half a year in contrast to one month. Optionally, control 140 is programmed to require charging based on the worst case interval, for example every month. In an exemplary embodiment of the invention, battery 160 can be charged additively without affecting its ability to hold a charge. Optionally, when charging, implant 120 notifies charger 110 when battery 160 reaches its maximum capacity and optionally stops charging, thus no harm is incurred in attempting to charge more frequently.

In some embodiments of the invention, in addition to the recharging that is initiated by the charger, if an extreme occurrence occurs, which might consume the charge in battery 160, the patient is required to initiate the recharging process to charge implant 110 and not wait for an indication from charger 110, since charger 110 is unaware of the occurrence, which requires shortening the interval for charging. Optionally, the worst case charge interval mentioned above would prevent failure even if the user does not initiate the recharging process as a result of an extreme occurrence.

In an exemplary embodiment of the invention, battery 160 is selected from a type that can be charged at any time without leading to deterioration in its ability to hold a charge. However charger 110 is adaptable to handle other types of batteries. In an exemplary embodiment of the invention, battery 160 is of a type that should be recharged only upon reaching a certain level of depletion to maximize its ability to hold a charge (e.g. Nickel-Cadmium batteries). Optionally, when attempting to recharge, implant 120 notifies charger 110 if it is time to recharge or if battery 160 is not depleted enough. In some embodiments of the invention, charger 110 changes the interval for checking the status of battery 160 based on the determined status. Optionally, the interval is made shorter and shorter, requiring the user to deploy charger 110 and check if implant 120 is in a state when its battery 160 is below a minimum charge level but before it is completely drained. After recharging battery 160 a longer interval may be automatically selected again.

In an exemplary embodiment of the invention, charger 110 comprises a power supply 220. Optionally, power supply 220 is plugged into a standard household power outlet with a power cable 210. Power supply 220 supplies DC and AC current to the other elements of charger 110. In some embodiments of the invention charger 110 comprises backup battery 170 mentioned above, that supplies backup power so that charger 110 can keep track of time and activate an indication even when it is not plugged in.

In an exemplary embodiment of the invention, charger 110 comprises a converter 260 to supply current to a circuit 270 and to produce an electromagnetic field for transcutaneously charging battery 160.

In an exemplary embodiment of the invention, control 140 controls charger 110. Optionally, control 140 keeps track of the time to charge, alerts the user as described above, controls charging by turning circuit 270 on and off and receives communication from implant 120 via a wireless receiver 250.

In an exemplary embodiment of the invention, implant 120 comprises a receiving circuit 215, which receives electric power from the electromagnetic field produced by circuit 270. Optionally, circuits 215 and 270 comprise primary and secondary coils of an inductive charger. In an exemplary embodiment of the invention, circuit 215 is connected to a rectifier 225 to convert the AC current induced in circuit 215 to DC current in order to charge battery 160.

In an exemplary embodiment of the invention, implant 120 comprises a meter 245 (e.g. a voltage meter), which keeps track of the level of charge in battery 160. Optionally a sensor 235 (e.g. a resistance meter which measures resistance that is affected by temperature) keeps track of the temperature level at one or more selected points, inside or on the surface of implant 120. Optionally, the selected points are chosen by selecting points which give an average representing the temperature throughout the implant. Alternatively, the points are selected according to the importance of the point, for example at points of contact with tissue that must not exceed a specific temperature.

In an exemplary embodiment of the invention, sensor 235 and meter 245, give indication to a wireless transmitter 255. Optionally, an indication from sensor 235 may be that the temperature is below a maximum value or has reached a maximum value. In some embodiments of the invention, the indication may represent an absolute temperature value. In some embodiments of the invention, the indication from meter 245 may be that the battery is charged to a maximum level or is still below this level or may be a value representing a charge level. Transmitter 255 transmits the information to receiver 250, which acts in response to the information.

In some embodiments of the invention, transmitter 255 begins transmitting when power is supplied to implant 120 by charger 110 so that transmissions do not consume charge from battery 160. Optionally, the transmissions update charger 110 with the charge level of battery 160 and optionally with the temperature inside the implant. In some embodiments of the invention, transmitter 255 continues to transmit periodically (e.g. every 1, 5, 10, 30, 60 or 300 seconds) while charger 110 is deployed to supply power to implant 120. Alternatively, transmitter 255 transmits values when there is a change from the previous value.

In some embodiments of the invention, transmitter 255 and receiver 250 both can transmit and receive information in order to allow implementation of more complex coordination between them, for example querying the implant directly for information. In an exemplary embodiment of the invention, communication between charger 110 and implant 120 is only enabled at short distances, for example up to 10 or 20 cm between them, such as while charger 110 is deployed, in order to minimize power consumption. Alternatively, implant 120 can transmit information to charger 110 from a long distance, for example 5 meters or 10 meters, so that charger 110 does not need to be deployed in order to know the charge level of implant 120.

In some embodiments of the invention, charger 110 detects when it is not optimally positioned with respect to implant 120, for recharging. This is done, for example, using any of the methods described in US 2005/0075696. Optionally, control 140 in charger 110 detects when the charger is not optimally positioned by the fact that the power load on circuit 270, due to its interaction with circuit 215, is lower than it should be, or by the fact that the current induced in circuit 215 is lower than it should be for a given current in circuit 270. If the current in circuit 215 is used for this purpose, then optionally the current is measured by a current meter within implant 120, and the information is communicated to charger 110 by transmitter 255 and receiver 250. Alternatively, the current in circuit 215 is measured remotely, from inside charger 110 or from elsewhere outside the body, and communicated to control 140.

Optionally, control 140 causes indicator 150, or another indicator, to give an indication, for example an audible or visible signal, which indicates to the patient or to another user when the charger is not positioned properly, so that the position of the charger can be adjusted. Additionally or alternatively, information about the non-optimal position of the charger is used by control 140 to increase the current in circuit 270, or to increase the charging time, or both, so that battery 160 will be fully charged. However, adjusting the position of charger 110 has the potential advantages that less energy may be used to charge battery 160, less heat may be generated, and battery 160 may be charged more quickly.

In some embodiments of the invention, communication between implant 120 and recharger is 110 is accomplished by modulating the current in 215 and 270, instead of, or in addition to, using transmitter 255 and receiver 250.

In some embodiments of the invention, meter 245 activates an alarm, for example a beeper or vibrator, located inside the body with implant 120 or outside the body, when the charge on battery 160 falls below a given level, in order to notify the patient that the implant should be recharged. Optionally, meter 245 measures the charge level of battery 160 at regular intervals, or continuously.

Figure 3:
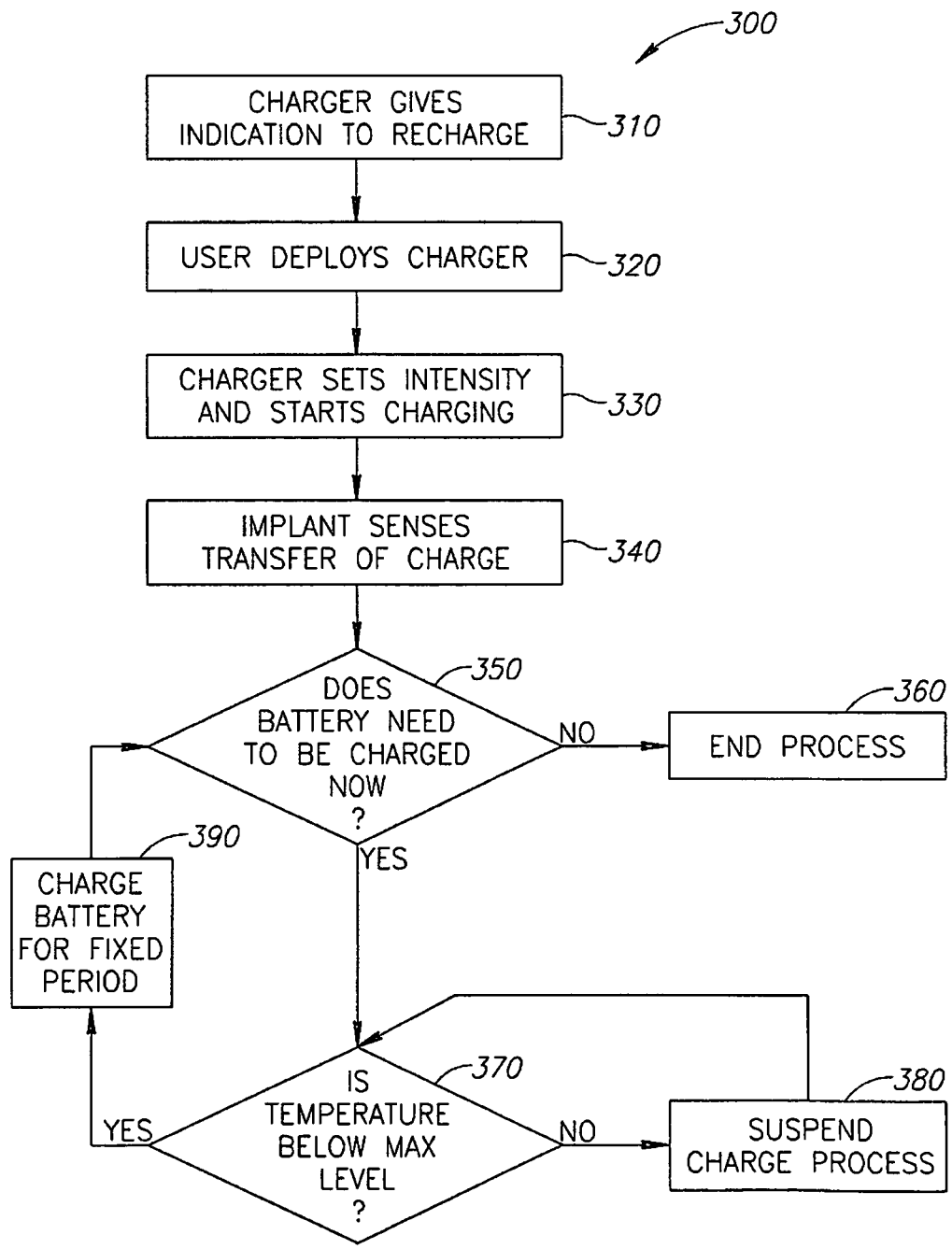
FIG. 3 is a flow diagram of a method of use of the transcutaneous charge system, according to an exemplary embodiment of the invention.

FIG. 3 is a flow diagram of a method 300 of use of transcutaneous charge system 100, according to an exemplary embodiment of the invention. In an exemplary embodiment of the invention, charger 110 gives indication (310) to a user that it is time to recharge implant 120. In some embodiments of the invention, the indication may start at a low frequency (e.g. a beep once an hour or half an hour) and increase in frequency (e.g. a beep every minute or every 10 seconds) until the user deploys (320) system 100 and recharges battery 160. In an exemplary embodiment of the invention, once charger 110 is deployed it sets an initial current intensity level and starts charging (330).

In some embodiments of the invention, the patient or another user activates a switch 155 on indicator 150 in order to start the charging process. Alternatively, charger 110 comprises a sensor 265 which detects implant 120 (e.g. a magnetic detector) and initiates transfer of charge when the distance between charger 110 and implant 120 is below a pre-selected value (e.g. 3, 5, 10 or 15 cm).

In an exemplary embodiment of the invention, implant 120 senses (340) the transfer of charge and starts monitoring the charging process. Optionally, meter 245 checks the charge of battery 160 (e.g. potential) to determine if battery 160 needs to be charged (350).

If sensor 245 finds that battery 160 does not need to be currently charged, transmitter 255 notifies receiver 250 to suspend the charging process. Optionally, an indication will be precluded (e.g. beeping turned off) or an indication will be given (e.g. a led is turned on), indicating termination of the process (360) since battery 160 does not need to be charged at the present time.

If battery 160 needs to be charged, sensor 235 will give an indication of the temperature near implant 120 to ensure that the charging process does not cause the person to get burnt from overheating. If the sensed temperature is below a maximum level (370) (e.g. 39° C. or 40° C.) charger 110 continues charging the battery for a period of time (390), and then again checks whether the battery needs charging (350). The period of time is optionally short enough so that, if the temperature sensed by sensor 235 is below the maximum level at the beginning of the period, then it will not rise to a dangerous level by the end of the period. Otherwise implant 120 communicates to control 140 in charger 110, causing charger 110 to suspend the charging process (380), until the temperature goes below the maximum level. The maximum temperature is optionally selected to prevent damage to internal organs or tissue as a result of overheating before suspension of the charging process takes affect.

In some embodiments of the invention, a temperature sensor on the skin, outside the body adjacent to implant 120, communicates to control 140 in charger 110, causing charger 110 to suspend the charging process until the temperature of the skin goes below a maximum level, optionally selected to be indicative of a safe level of heating. In some embodiments of the invention, there are two temperature sensors, sensor 235 in implant 120, and a sensor on the skin, and charging is suspended if either one of the sensors measures too high a temperature, or only if both sensors measure too high a temperature.

In some embodiments of the invention, temperature sensor 235, and/or another temperature sensor on the skin, communicates to control 140 if the measured temperature rise during recharging is less than expected, which may indicate a fault with the recharging process, for example that charger 110 is not positioned properly, or that circuit 215 or battery 160 has too high an impedance for some reason, which could possibly indicate failure or incipient failure of circuit 215 or battery 160. Control 140 then signals an indicator, such as indicator 150, to indicate this problem to the patient and/or to medical personnel, who can decide whether to replace the implant, or to continue to monitor the situation.

In some embodiments of the invention, a low charging current, for example 5% or 10% or 20% of a maximum charging rate for battery 160, is used for charging battery 160. A suitable battery, for example, is the model R1 1098 lithium ion battery made by Greatbatch®, Inc., which has a full charge of 550 mA hours, and a maximum charging rate of 275 mA. A low charging current allows a more continuous charging rate, since heat dissipation from the implant would exceed the heating caused by charging at a low current. However a low charging current requires a long charge time, for example 5 hours or longer, which is an annoyance for the patient. In an exemplary embodiment of the invention, a higher charging current is used, for example 25% or 50% or more of the maximum charging rate. However, a higher charging current causes greater heating, which according to an exemplary embodiment of the invention, leads to suspension of the charging process until the temperature goes down. In some embodiments of the invention, the use of one or more cooling pads allows lengthening the duty cycle of the charging process and speeding up the charging process.

Figure 4:
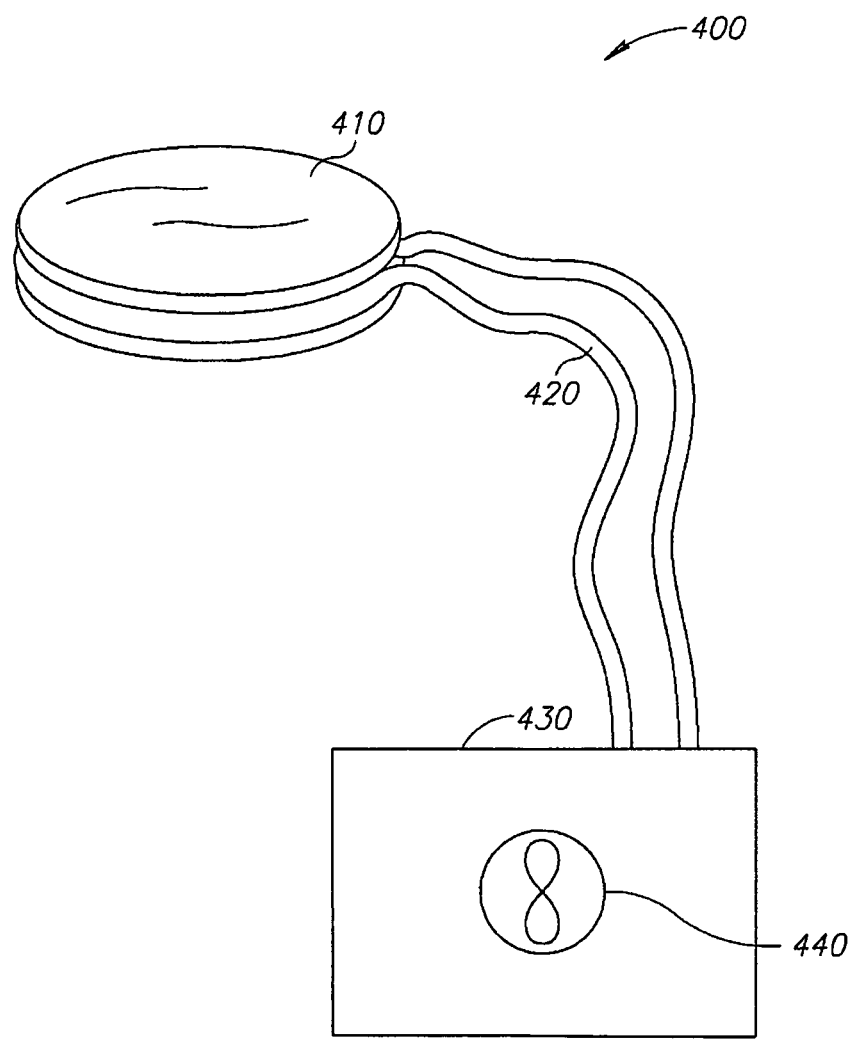
FIG. 4 is a schematic illustration of a dynamic cooling pad, according to an exemplary embodiment of the invention.

FIG. 4 is a schematic illustration of a dynamic cooling pad system 400, according to an exemplary embodiment of the invention. In an exemplary embodiment of the invention, a dynamic cooling system 400 is used to cool down the user by positioning dynamic cooling pad 410 on the user's skin in the vicinity of implant 120. In an exemplary embodiment of the invention, a dynamic cooling pad 410 is positioned between charger 110 and the user's skin to help dissipate the heat that builds up at the implant during the charging process and heat from charger 110. In an exemplary embodiment of the invention a cooling system 430 (e.g. an Intel™ processor water cooler kit such as is commonly used in some personal computers) is used to cool down a liquid and pump it into cooling pad 410. Optionally, dynamic cooling pad 410 is connected by two tubes 420 to cooling system 430. Cooled liquid is pumped into dynamic cooling pad 410 and the warmer liquid is pushed out into tube 420 toward cooling system 430. Cooling system 430 uses a fan 440 or other methods (e.g. expansion of compressed gas) to cool down the liquid. The effect of cooling system 430 is to maintain a lower temperature in the liquid without replacing the pad.

In an exemplary embodiment of the invention, cooling pad 410 comprises two silicone sheets forming a void between them. In an exemplary embodiment of the invention, the silicone sheets are prepared with a width and length of approximately 5-15 cm, to cover the area above implant 120. Optionally, the thickness of the sheets is between 0.1 mm to 5 mm.

In some embodiments of the invention, the two silicone sheets of cooling pad 410 are separated by a tube around the circumference of the silicone sheets. Optionally, the tube is adhesively attached to the silicone sheets forming a void that can accommodate a liquid to dissipate heat. Alternatively, the pad may be cast entirely from silicone or from other materials (e.g. rubber). In some embodiments of the invention pad 410 is formed entirely from a tube wound around and glued together to form a surface.

It will be appreciated that the above described methods may be varied in many ways, including, changing the materials used in the system. It should also be appreciated that the above described description of methods and apparatus are to be interpreted as including apparatus for carrying out the methods and methods of using the apparatus.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art.

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims. When used in the following claims, the terms "comprise", "include", "have" and their conjugates mean "including but not limited to".

The invention claimed is:

1. A transcutaneous charging device for charging an implant comprising:
   a power input;
   a conversion circuit to convert power from said power input to transcutaneously charge said implant;
   a control located in said transcutaneous charging device; and
   an indication element;
   wherein said control located in said transcutaneous charging device is programmed to initiate an indication to charge said implant, using said indication element, said initiating an indication by said control located in said transcutaneous charging device being performed before said implant is charged,
   the charging device further comprising a wireless receiver and wherein said indication is stopped after deploying said charging device and receiving a signal from said implant by said wireless receiver;
   said device further comprising a sensor configured to detect a signal associated with a distance between said charging device and the implant, said charging device configured to initiate transfer of charge to the implant when the signal associated with the distance indicates a distance which is less than a preselected distance;
   said sensor additionally configured to detect a positioning of said charging device relative to the implant, said control configured to at least one of increase a current in said conversion circuit and increase a charging time in response to said sensor detecting that a positioning of said charging device relative to the implant is not optimal.

2. A device according to claim 1, wherein said indication is initiated periodically.

3. A device according to claim 1, wherein said indication is initiated on specific dates.

4. A device according to claim 1, wherein said indication, when activated, is continuous.

5. A device according to claim 1, wherein said indication, when activated, is intermittent.

6. A device according to claim 2, wherein said signal received from said implant by said wireless receiver is supplied by said implant after it is recharged.

7. A device according to claim 1, wherein said indication element comprises a display, an audio transmitter, and a mobile telephone transmitter.

8. A device according to claim 1, comprising a battery backup.

9. A device according to claim 1 wherein said indication gives an indication of a charge status of a battery in the implant.

10. A device according to claim 1 wherein said indication element gives an indication to a user that it is time to charge the battery.

11. A device according to claim 1, wherein said charging device is configured to charge said implant while being shielded from direct contact with a user.

12. A device according to claim 1, wherein said deploying includes placing said charging device on a patient's skin facing the implant.

13. A device according to claim 1, wherein said deploying includes placing said charging device on a patient's skin as close as possible to the implant.

14. A device according to claim 1, wherein said charging device is configured to give an indication to the implant, said indication including a query for information related to the implant.

15. A device according to claim 14, wherein said information is selected from a charge level of a battery in the implant and a temperature inside the implant.

16. A device according to claim 1, wherein said charging device is configured to give an indication to said control.

17. A device according to claim 16, wherein said indication to said control is related to a non-optimal position of said charging device relative to the implant.

18. A device according to claim 1, wherein said implant is configured to give an indication of at least one of the temperature of said implant and a temperature of skin of a user.

19. A device according to claim 1, said control additionally configured to initiate an indication that the positioning of said charging device relative to the implant is not optimal.

20. A device according to claim 1, wherein said control is configured to receive a signal from the implant and is configured to actuate said indication element to provide an indication to charge said implant, using said indication element.

* * * * *